US012066312B2

(12) United States Patent
Provost et al.

(10) Patent No.: US 12,066,312 B2
(45) Date of Patent: Aug. 20, 2024

(54) METHOD AND DEVICE FOR DETERMINING A FLOW RATE AND/OR A CONCENTRATION OF PARTICLES OF A FLUID

(71) Applicants: AENITIS TECHNOLOGIES, Mitry-Mory (FR); INSERM (INSTITUT NATIONAL DE LA SANTÉ ET DE LA RECHERCHE MÉDICALE), Paris Cedex (FR); CENTRE NATIONAL DE LA RECHERCHE SCIENTIFIQUE, Paris (FR); ÉCOLE SUPÉRIEURE DE PHYSIQUE ET DE CHIMIE INDUSTRIELLES DE LA VILLE DE PARIS, Paris (FR)

(72) Inventors: Jean Provost, Montréal (CA); Jérémie Gachelin, Arcueil (FR); Baptiste Pialot, Pantin (FR); Olivier Couture, Issy-les-Moulineaux (FR); Emmanuel Vincent, Mitry-Mory (FR)

(73) Assignees: AENITIS TECHNOLOGIES, Mitry-Mory (FR); INSERM (INSTITUT NATIONAL DE LA SANTÉ ET DE LA RECHERCHE MÉDICALE), Paris (FR); CENTRE NATIONAL DE LA RECHERCHE SCIENTIFIQUE, Paris (FR); ÉCOLE SUPÉRIEURE DE PHYSIQUE ET DE CHIMIE INDUSTRIELLES DE LA VILLE DE PARIS, Paris (FR)

( * ) Notice: Subject to any disclaimer, the term of this patent is extended or adjusted under 35 U.S.C. 154(b) by 562 days.

(21) Appl. No.: 17/297,689

(22) PCT Filed: Oct. 18, 2019

(86) PCT No.: PCT/EP2019/078438
§ 371 (c)(1),
(2) Date: May 27, 2021

(87) PCT Pub. No.: WO2020/126152
PCT Pub. Date: Jun. 25, 2020

(65) Prior Publication Data
US 2021/0396559 A1 Dec. 23, 2021

(30) Foreign Application Priority Data

Dec. 21, 2018 (EP) .................................. 18306815

(51) Int. Cl.
*G01F 1/06* (2006.01)
*G01F 1/663* (2022.01)
*G01N 15/06* (2024.01)
*G01N 15/01* (2024.01)

(52) U.S. Cl.
CPC ............. *G01F 1/663* (2013.01); *G01N 15/06* (2013.01); *G01N 2015/012* (2024.01)

(58) Field of Classification Search
USPC ..................................................... 73/861.25
See application file for complete search history.

(56) References Cited

U.S. PATENT DOCUMENTS 3,498,290 A * 3/1970 Shaw ...................... G01F 1/663
367/90
3,554,030 A * 1/1971 Peronneau .............. G01F 1/663
367/90

(Continued)

FOREIGN PATENT DOCUMENTS

EP 2837327 A1 2/2015

OTHER PUBLICATIONS

International Search Report issued on Jan. 27, 2020 in corresponding application No. PCT/EP2019/078438; 4 pgs.

(Continued)

*Primary Examiner* — Clayton E. LaBalle
*Assistant Examiner* — Warren K Fenwick
(74) *Attorney, Agent, or Firm* — Maier & Maier, PLLC

(57) ABSTRACT

A method for determining a flow rate and/or a concentration of particles of a fluid flowing in a chamber, which includes (Continued)

the steps of: producing an ultrasound beam of a given frequency with a first transducer such that all fluid components traveling through an intersection region between the ultrasound beam and the chamber are insonated by the first transducer; receiving Doppler-shifted ultrasound signals generated by the fluid components in the insonated region of the chamber with a second transducer; acquiring the ultrasound signals received by the second transducer during an acquisition time; obtaining a Doppler Power Spectrum of the acquired ultrasound signals; and determining the flow rate and/or the concentration of particles of the fluid by adjustment between, on the one hand, the obtained Doppler Power Spectrum and, on the other hand, a model of the Doppler Power Spectrum.

14 Claims, 7 Drawing Sheets

(56) References Cited

U.S. PATENT DOCUMENTS

| | | | | |
|---|---|---|---|---|
| 3,977,247 A * | 8/1976 | Hassler | ............... | A61B 8/06 73/861.25 |
| 4,062,237 A * | 12/1977 | Fox | ............... | A61B 8/06 600/447 |
| 4,067,236 A * | 1/1978 | Hottinger | ............... | A61B 8/06 73/861.25 |
| 4,431,936 A * | 2/1984 | Fu | ............... | G10K 11/26 310/369 |
| 4,519,260 A * | 5/1985 | Fu | ............... | G01F 1/662 73/861.25 |
| 4,807,636 A * | 2/1989 | Skidmore | ............... | A61B 8/06 600/456 |
| 5,986,553 A | 11/1999 | Young | | |
| 6,601,459 B1 * | 8/2003 | Jenni | ............... | G01F 1/663 73/861.25 |
| 2008/0163700 A1 | 7/2008 | Huang | | |
| 2014/0046606 A1 | 2/2014 | Torp et al. | | |
| 2018/0256025 A1 | 9/2018 | Yi et al. | | |

OTHER PUBLICATIONS

Vilkomerson David et al: "Finding the peak velocity in a flow from its doppler spectrum", IEEE Transactions on Ultrasonics, Ferroelectrics and Frequency Control, IEEE, US, vol. 60, No. 10, Oct. 1, 2013 (Oct. 1, 2013), pp. 2079-2088, 10 pgs.

* cited by examiner

METHOD AND DEVICE FOR DETERMINING A FLOW RATE AND/OR A CONCENTRATION OF PARTICLES OF A FLUID

FIELD

The present invention relates to a method for determining a flow rate and/or a concentration of particles of a fluid flowing in a chamber, using Doppler-shifted ultrasound echoes. The invention also relates to a measurement device for determining a flow rate and/or a concentration of particles of a fluid flowing in a chamber. The method and device of the invention may be used for the determination of a flow rate and/or a concentration of particles of any heterogenous fluid, emulsion, or more generally any fluid comprising particles, for example cell suspensions such as whole blood, bone marrow, cerebrospinal fluids, or mineral suspensions such as mine slurry or mud.

BACKGROUND

Implementation of emerging fluid techniques, such as acoustophoretic blood fractionation within standardized medical devices, requires non-invasive methods for evaluating and controlling processes. Such methods should be selected to provide reliable estimations of physical parameters, without compromising the integrity of the fluid and its components. Among the parameters to be monitored, fluid flow rate is of particular importance, in particular to determine if the fluid flow is steady.

There exist several techniques allowing accurate and robust estimation of the flow rate of a fluid. Examples of known techniques include optical or electromagnetic techniques. Ultrasound techniques, and in particular techniques based on the Doppler effect, have the advantage of being non-invasive, inexpensive and easy to implement in various devices.

According to the Doppler effect equation in the case of a stationary fluid flow within a chamber, the measurement of the maximum frequency of the Doppler Power Spectrum (DPS), generated by the movement of particles of the fluid, allows a simple estimation of the maximum velocity of the fluid. The flow rate of the fluid can then be calculated from this estimation via the Hagen-Poiseuille equation.

However, due to intrinsic spectral broadening, accurate estimation of the maximum frequency of the Doppler Power Spectrum is a non-trivial problem, even in a controlled environment with limited sources of errors. Accordingly, estimation of the flow rate and other relevant parameters, such as the concentration of fluid components, is not accurate.

It is these drawbacks that the invention is intended more particularly to remedy by proposing a method and a device making it possible to accurately determine a flow rate and/or a concentration of particles of a fluid flowing in a chamber, while being easy to use and implement, without the drawbacks of the prior art.

SUMMARY

For this purpose, according to one aspect, a subject of the invention is a method for determining a flow rate of a fluid flowing in a chamber and a concentration of particles of the fluid, the method comprising steps of:

producing an ultrasound beam, of a given frequency selected in the scattering frequency range of said particles, by means of a first transducer, in such a way that all fluid components traveling through an intersection region I between the ultrasound beam and the chamber are insonated by the first transducer;

receiving Doppler-shifted ultrasound signals generated by the fluid components in said insonated region of the chamber by means of a second transducer;

acquiring the ultrasound signals received by the second transducer during an acquisition time;

obtaining a Doppler Power Spectrum of the acquired ultrasound signals;

determining the flow rate of the fluid flowing in the chamber and the concentration of said particles of the fluid in the insonated region by adjustment between, on the one hand, the obtained Doppler Power Spectrum and, on the other hand, a model expressing the Doppler Power Spectrum as a function of the flow rate of the fluid in the insonated region of the chamber, the concentration of said particles of the fluid in the insonated region, the cross-sectional area of the chamber taken perpendicular to the flow direction, the width of the intersection between the ultrasound beam and the chamber taken parallel to the flow direction The method of the invention makes it possible to determine the flow rate of the fluid in a simple manner by adjustment, or "fitting", between the measured Doppler Power Spectrum (DPS) and a modeled DPS which is expressed as a function of the flow rate of the fluid, the cross-sectional area of the chamber and the width of the intersection between the ultrasound beam and the chamber. Since the cross-sectional area of the chamber and the width of the intersection between the ultrasound beam and the chamber can be fixed experimentally, the adjustment between the acquired DPS and the modeled DPS provides direct access to the flow rate of the fluid.

In an advantageous manner, the method of the invention has a limited number of steps and is easy to implement. The calculation steps of the method, in particular for the adjustment between the acquired DPS and the modeled DPS, may be implemented with the aid of any appropriate calculation means. In particular, the calculation means, which may be a computer or any electronic calculation unit, is advantageously connected to an acquisition system for acquiring the measurements required by the method and comprises calculation means for executing all or part of the calculation steps of the method on the basis of the acquired measurements. The reliability of the method of the invention for estimating fluid flow rates has been proven to be strong, even at low flow rates of the order of 0.1 mL/min.

According to one embodiment, the method is such that the Doppler-shifted ultrasound signals are generated by the fluid components in said insonated region of the chamber 2 while the concentration of said particles of the fluid in the insonated region has a known concentration value, and the method comprises a step of determining the flow rate of the fluid flowing in the chamber by adjustment between, on the one hand, the obtained Doppler Power Spectrum and, on the other hand, a model expressing the Doppler Power Spectrum as a function of the flow rate of the fluid in the insonated region of the chamber, the concentration of said particles of the fluid in the insonated region, the cross-sectional area of the chamber taken perpendicular to the flow direction, the width of the intersection between the ultrasound beam and the chamber taken parallel to the flow direction, with the concentration of said particles of the fluid in the insonated region being fixed at said known concentration value.

According to another aspect, a subject of the invention is a method wherein the Doppler-shifted ultrasound signals are generated by the fluid components in said insonated region of the chamber while the flow rate of the fluid flowing in the chamber has a known flow rate value, and the method comprises a step of determining the concentration of said particles of the fluid in the insonated region by adjustment between, on the one hand, the obtained Doppler Power Spectrum and, on the other hand, a model expressing the Doppler Power Spectrum as a function of the flow rate of the fluid in the insonated region of the chamber, the concentration of said particles of the fluid in the insonated region, the cross-sectional area of the chamber taken perpendicular to the flow direction, the width of the intersection between the ultrasound beam and the chamber taken parallel to the flow direction, with the flow rate of the fluid in the insonated region of the chamber being fixed at said known flow rate value.

According to this aspect, the invention makes it possible to determine the flow rate and the concentration of particles of the fluid in a simple manner by adjustment, or "fitting", between the measured Doppler Power Spectrum (DPS) and a modeled DPS which is expressed as a function of the flow rate of the fluid, the concentration of the particles of the fluid in the insonated area, the cross-sectional area of the chamber and the width of the intersection between the ultrasound beam and the chamber. Since the cross-sectional area of the chamber and the width of the intersection between the ultrasound beam and the chamber can be fixed experimentally, the adjustment between the acquired DPS and the modeled DPS provides direct access to the flow rate and particle concentration of the fluid. The method advantageously has a limited number of steps and can be easily implemented with the aid of appropriate calculation means.

The method of the invention, in any of its aspects described above, is suitable for determining flow rates as low as 0.1 mL/min. In particular, the sensitivity of the method of the invention at low flow rates is high compared to that of methods known from the prior art.

According to another aspect, a subject of the invention is a method comprising steps of:
  calculating the integral of the obtained Doppler Power Spectrum over a frequency range including the maximum frequency of the Doppler Power Spectrum;
  determining the concentration of particles of the fluid in the insonated region by adjustment between the integral of the obtained Doppler Power Spectrum and a model expressing the integral of the Doppler Power Spectrum as a function of the concentration of said particles of the fluid in the insonated region, such as a calibration function.

According to this aspect, the invention makes it possible to determine the concentration of particles of a fluid by adjustment, or "fitting", between the integral of the Doppler Power Spectrum and the model. This adjustment provides direct access to the concentration of particles of the fluid.

In a specific embodiment, the method is such that the fluid is blood and a volumic concentration H (hematocrit) of red blood cells is determined by calculating the maximum frequency of the obtained Doppler Power Spectrum.

According to one embodiment, the adjustment between the obtained Doppler Power Spectrum and the model, or between the integral of the Doppler Power Spectrum and the model, is realized using an optimization algorithm. In particular, the optimization algorithm may comprise a minimization of a cost function expressed with a predefined norm. Such an optimization algorithm is simple to use in the context of the invention, the flow rate and/or the particle concentration being the parameters for which the cost function is minimum.

For the method of the invention, in any of its aspects described above, the Doppler Power Spectrum of the acquired ultrasound signals can be obtained using a demodulation method.

The invention can be implemented for any heterogenous fluid, emulsion, or any fluid comprising particles, for example for cell suspensions such as whole blood, bone marrow, or cerebrospinal fluids or for mineral suspensions such as mine slurry or mud. The method of the invention as described above is particularly suitable for determining the flow rate and/or the concentration of particles of opaque fluids, for which it is not possible to use optical methods for the determination of these parameters.

The method according to the invention is particularly suitable for determining the flow rate and/or the concentration of particles of a fluid whose flow in the chamber can be modelized. For example, the method of the invention is particularly suitable for determining the flow rate of a fluid having a stationary flow, for which the velocity profile can be modelized. More generally, the method is suitable for any laminar flow of a fluid in a chamber.

The invention further relates to a method for determining a concentration of a first group of particles and a concentration of a second group of particles of a fluid, the particles of the first group and the particles of the second group being particles having scattering frequency ranges at least partially not overlapping, the method comprising:
  determining the concentration of the first group of particles according to the method of the invention, by producing a first ultrasound beam of a first given frequency;
  determining the concentration of the second group of particles or the total concentration of the first and second groups of particles according to the method the invention, by producing a second ultrasound beam of a second given frequency.

In this way, it is possible to determine the concentrations of groups of particles having different scattering frequencies, by changing the frequency of the ultrasound beam. Thanks to the sensitivity of the groups of particles to different Doppler frequencies, the concentration of the first group of particles can be obtained at the first frequency and the concentration of the second group of particles can be obtained at the second frequency, either directly or from a comparison between the total concentration of particles and the concentration of the first group of particles. Of course, the method of the invention can be applied to fluids comprising more than two groups of particles.

According to one embodiment, the fluid is blood, the particles of the first group are red blood cells and the particles of the second group are platelets, wherein the first frequency, which is suitable for the determination of the volumic concentration of red blood cells, is lower than the second frequency, which is suitable for the determination of the total volumic concentration of red blood cells and platelets. The first frequency and the second frequency are in the range 0-100 MHz.

The volumic concentration of platelets can be deduced from the total volumic concentration of red blood cells and platelets on the one hand, and the volumic concentration of red blood cells on the other hand. The invention makes it possible to determine the volumic concentration of platelets based on a comparison between a volumic concentration obtained at a lower ultrasound frequency and a volumic concentration obtained at a higher ultrasound frequency.

Another subject of the invention is a computer program comprising instructions for the implementation of the calculation steps of a method as described above when the program is executed by a computer.

Another subject of the invention is a non-transitory computer readable medium comprising instructions for the implementation of the calculation steps of a method as described above when the instructions are executed by a computer.

According to another aspect, a subject of the invention is a measurement device for determining a flow rate of a fluid flowing in a chamber and a concentration of particles of the fluid, comprising:
- a first transducer configured to produce an ultrasound beam of a given frequency selected in the scattering frequency range of said particles, in such a way that all fluid components traveling through an intersection region between the ultrasound beam and the chamber are insonated by the first transducer,
- a second transducer, arranged at a Doppler angle to the flow direction and configured to receive Doppler-shifted ultrasound signals generated by the fluid components in said insonated region of the chamber;
- an acquisition module for acquiring the ultrasound signals received by the second transducer during an acquisition time;
- a calculation module configured to calculate a Doppler Power Spectrum of the ultrasound signals acquired by the acquisition module and to determine the flow rate of the fluid flowing in the chamber and the concentration of said particles of the fluid by adjustment between the calculated Doppler Power Spectrum and a model expressing the Doppler Power Spectrum as a function of the flow rate of the fluid in the insonated region of the chamber, the concentration of said particles of the fluid in the insonated region, the cross-sectional area of the chamber taken perpendicular to the flow direction, the width of the intersection between the ultrasound beam produced by the first transducer and the chamber taken parallel to the flow direction.

Such a measurement device makes it possible to determine the flow rate of the fluid in a simple manner by adjustment, or "fitting", between the measured Doppler Power Spectrum (DPS) and a modeled DPS which is expressed as a function of the flow rate of the fluid, the cross-sectional area of the chamber and the width of the intersection between the ultrasound beam and the chamber. As the cross-sectional area of the chamber and the width of the intersection between the ultrasound beam and the chamber can be fixed experimentally, the adjustment between the acquired DPS and the modeled DPS provides direct access to the flow rate of the fluid.

According to another aspect, the measurement device is such that the first transducer is configured to produce an ultrasound beam selectively at a first frequency and at a second frequency distinct from the first frequency, at least one of the first and second frequencies being selected in a non-overlapping portion between the scatterering frequency ranges of two groups of particles.

According to another aspect, a subject of the invention is a separation device comprising a cavity configured to receive a flow of a fluid comprising particles, at least one inlet at a first end of the cavity, at least two outlets at a second end of the cavity, comprising at least one concentrate-outlet and at least one filtrate-outlet, wherein the separation device further comprises at least one measurement device.

As a non-limiting example, such a separation device may be applied for blood fractionation. Such a separation device may be, in particular, an acoustophoretic separation device, a centrifugation device, a magnetic separation device.

DETAILED DESCRIPTION

The following detailed description will be better understood when read in conjunction with the drawings. For the purpose of illustrating, the device is shown in the preferred embodiments. It should be understood, however that the application is not limited to the precise arrangements, structures, features, embodiments, and aspect shown. The drawings are not drawn to scale and are not intended to limit the scope of the claims to the embodiments depicted. Accordingly, it should be understood that where features mentioned in the appended claims are followed by reference signs, such signs are included solely for the purpose of enhancing the intelligibility of the claims and are in no way limiting on the scope of the claims.

Figure 1:
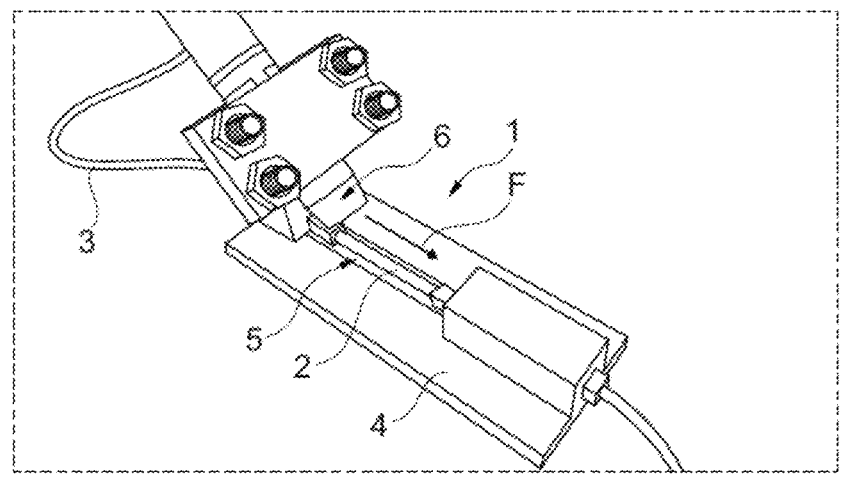
FIG. 1 is a partial perspective view of a measurement device according to an embodiment of the invention.

An example of a measurement device 1 according to the invention is shown partially in FIG. 1. The measurement device 1 comprises a chamber 2, formed by a portion of a tube 3, which is connected to a fluid source in such a way that the fluid can flow through the chamber 2, for example in the direction indicated by the arrow F in FIG. 1. By way of non-limiting example, the fluid flowing in the chamber 2 is blood.

The measurement device 1 also includes a base 4 with an open window 5. The tube 3 passes along the base 4 and is fixed to it so that the chamber 2 is situated facing the window 5. The measurement device 1 further comprises a probe 6, including a first transducer 61 and a second transducer 62 (shown schematically in FIG. 3), fixed to the base 4 with a Doppler angle θ relative to the direction F of the fluid flow.

The first transducer 61, which is an emitting transducer, is connected to a generator module and configured to produce an ultrasound beam of a given frequency, in such a way that all fluid components traveling through an intersection region I (shown in FIG. 3) between the chamber 2 and the ultrasound beam are insonated. The window 5 represented in FIG. 1, which is optional, makes it possible to reduce unwanted reflections (false echoes) of the ultrasound beam.

In one embodiment, the first transducer 61 is configured to produce an ultrasound beam selectively at a first frequency and at a second frequency distinct from the first frequency, at least one of the first and second frequencies being selected in a non-overlapping portion between the scattering frequency ranges of two groups of particles of the fluid. The first frequency and the second frequency are typically in the range 0-100 MHz.

The second transducer 62, which is a receiving transducer, is connected to an acquisition module (not shown) for acquiring the ultrasound signals received by the second transducer. The measurement device 1 further includes a calculation module, which is not shown in the drawings. Said calculation module is configured to calculate a Doppler Power Spectrum (DPS) of the ultrasound signals acquired by the acquisition module connected to the second transducer 62.

The calculation module is configured to determine the flow rate of the fluid flowing in the chamber by adjustment between the calculated Doppler Power Spectrum (DPS) and a model expressing the Doppler Power Spectrum as a function of the flow rate of the fluid in the insonated region of the chamber 2, the cross-sectional area 2R of the chamber 2 and the width A of the intersection I between the ultrasound beam produced by the first transducer 61 and the chamber 2.

Alternatively, the calculation module may be configured to determine the flow rate of the fluid flowing in the chamber 2 and the concentration of a given group of particles of the fluid by adjustment between the calculated Doppler Power Spectrum (DPS) and a model expressing the Doppler Power Spectrum as a function of the flow rate of the fluid in the insonated region of the chamber 2, the concentration of said particles of the fluid, the cross-sectional area 2R of the chamber 2 and the width A of the intersection between the ultrasound beam produced by the first transducer 61 and the chamber 2.

Of course, in other embodiments, the chamber 2 may have a different shape, for example the chamber may have a rectangular cross section instead of a circular cross section.

Figure 2:
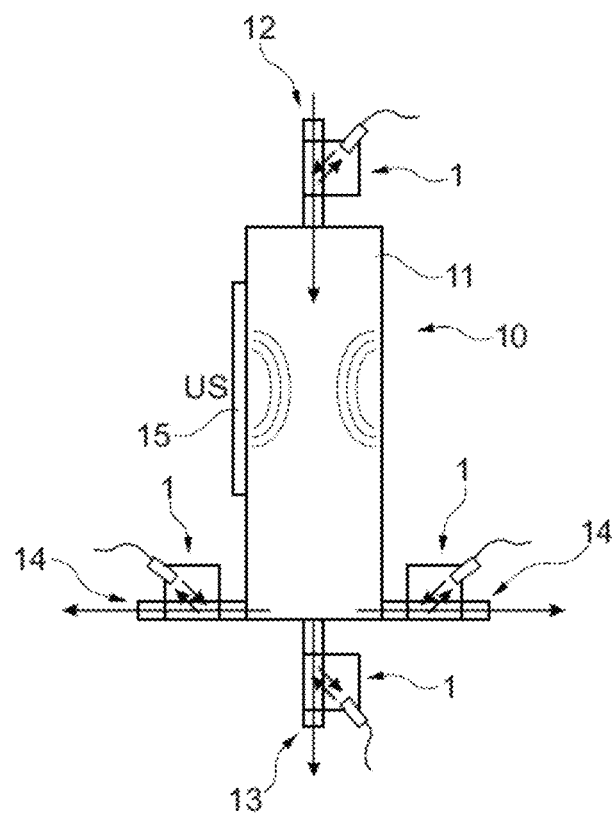
FIG. 2 is a schematic view of an acoustophoretic device including four measurement devices according to the invention.

FIG. 2 illustrates an acoustophoretic device 10 comprising four measurement devices 1 for measuring the flow rate and particle concentration of a fluid, respectively at the inlet 12 and the three outlets 13, 14 of the acoustophoretic device 10. The acoustophoretic device 10 comprises a channel 11 connected at one end to the inlet 12 and on the opposite end to a central outlet 13, called the concentrate-outlet, and to two peripheral outlets 14, called the filtrate-outlets.

The channel 11 is associated with at least one acoustic wave generator 15 for generating acoustic waves within the channel 11 between the inlet 12 and the outlets 13, 14, so as to induce acoustic separation of particles of a fluid flowing in the channel 11 from the inlet 12 towards the outlets 13, 14. In particular, in the case of blood flowing in the channel 11, it is possible to induce a migration of red blood cells toward the central concentrate-outlet 13 while the other blood particles, and in particular the platelets, tend to be equally distributed at the central concentrate-outlet 13 and the two peripheral filtrate-outlets 14.

The measurement devices 1 arranged at each of the inlet 12 and the outlets 13, 14 of the acoustophoretic device 10 make it possible to determine the flow rate and the concentration of particles of the fluid at different locations, e.g. so as to monitor the separation process. It is understood that the number and the positions of the measurement devices 1 may be different from those illustrated in FIG. 2. In particular, if in the embodiment of FIG. 2 the acoustophoretic device 10 includes four measurement devices 1, in other embodiments the number of measurement devices 1 may be different, for example three measurement devices 1 respectively arranged at the inlet 12, the central concentrate-outlet 13, and only one of the peripheral filtrate-outlets 14. Of course, the structure of the acoustophoretic device 10 as represented is only for illustration purpose and may be different in other embodiments of the invention.

Determination of the Flow Rate

In the following, a non-limitative embodiment of the method for determining the flow rate is described, for a fluid flowing in the chamber 2 of the measurement device 1. This example is given only for sake of illustration and should not in any case be considered as limiting the scope of the invention.

The method according to this embodiment includes steps of:
producing an ultrasound beam of a given frequency by means of the first transducer 61, in such a way that all fluid components traveling through the intersection region between the ultrasound beam and the chamber 2 are insonated;
receiving Doppler-shifted ultrasound signals generated by the fluid components in said insonated region of the chamber 2 by means of the second transducer 62;
acquiring the ultrasound signals received by the second transducer 62 during an acquisition time;
obtaining a Doppler Power Spectrum (DPS) of the acquired ultrasound signals;
determining the flow rate of the fluid flowing in the chamber 2 by adjustment between, on the one hand, the obtained Doppler Power Spectrum (DPS) and, on the other hand, a model expressing the Doppler Power Spectrum as a function of the flow rate of the fluid in the insonated region of the chamber 2, the cross sectional area of the chamber 2 and the width of the intersection between the ultrasound beam and the chamber 2.

Adjustment Model

The theoretical model as detailed below is based on the article of Vilkomerson et al. "Finding the peak velocity in a flow from its doppler spectrum" (IEEE Transactions on Ultrasonics, Ferroelectrics, and Frequency Control, Volume: 60, Issue: 10, 2079-2088).

Figure 3:
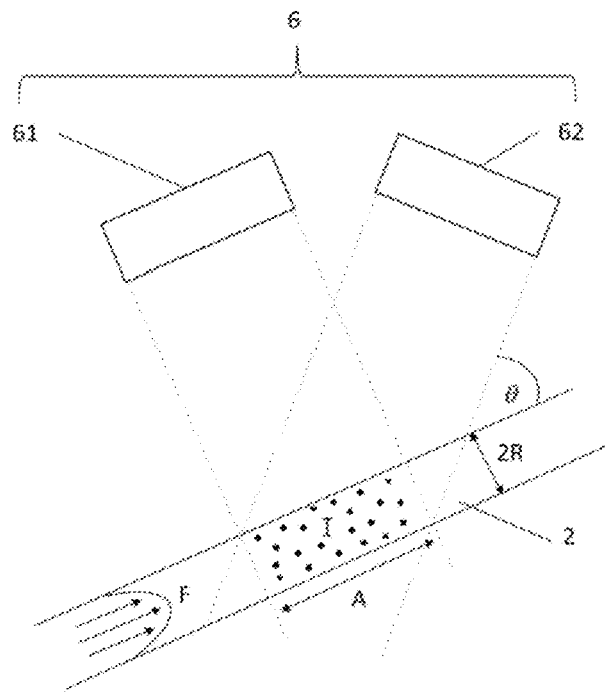
FIG. 3 is a schematic cross section of the measurement device of FIG. 1.

FIG. 3 is a schematic cross section of the measurement device 1 of FIG. 1. The chamber 2 is a portion of the tube 3 having a radius R. In this case, when a fluid, for example blood, flows through the chamber 2 in the indicated direction F, it is assumed to have a parabolic flow profile, which can be modelized.

Figure 4:
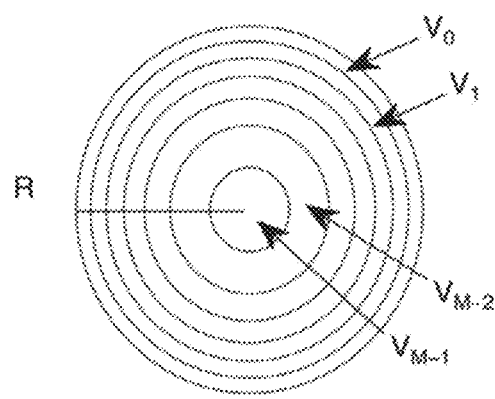
FIG. 4 is a schematic representation of a model of a fluid flow in a cross section of a cylindrical chamber, as described in Vilkomerson D, Ricci S, Tortoli P. (2013). Finding the peak velocity in a flow from its doppler spectrum. *IEEE Transactions on Ultrasonics, Ferroelectrics, and Frequency Control*, Volume: 60, Issue: 10, 2079-2088.

As shown in FIG. 4, it is proposed to divide the fluid flow in the chamber 2 into M concentric shells (or circles) of index m, whose centers coincide with the center of the tube. Each shell is then associated with a velocity $v_m$ which is the speed of the flow in the shell of index m. In this case, the maximum velocity $v_{M-1}$ is for the shell of index M−1 corresponding to the center of the tube, whereas the velocity $v_0$ of the shell of index 0 corresponding to the edge of the tube is zero.

In the intersection zone between the ultrasound beam and the tube, the theoretical Doppler Spectrum can be modeled as the sum of the contributions to the spectrum of each of the shells of index m, m being 0, ..., M−1, as a function of the following parameters:

$\rho_m$: The density of scatterers (diffusing particles) in the shell of index m. This density is directly related to the concentration of scatterers. For flow rate measurements, this parameter is assumed to be equal to 1.

A: The width of the intersection between the ultrasonic beam and the tube.

$tt_m$: The time that the diffusers spend in the ultrasound beam for the shell of index m. This time $tt_m$ is dependent on the velocity $v_m$ and A:

$$tt_m = \frac{A}{v_m}$$

$f_m$: The Doppler frequency corresponding to the velocity $v_m$ which is calculated using the equation of the ultrasonic Doppler effect:

$$f_m = \frac{v_m f_e \cos(\theta)}{c}$$

where $f_e$ is the ultrasound emission frequency, c is the speed of sound in the flow, θ is the Doppler angle.

$T_0$: The acquisition time of the Doppler signal.
N: The number of samples for the Doppler signal.
Fs: The sampling frequency.
R: The radius of the tube. It does not appear explicitly in the model but it is nevertheless essential since its knowledge is necessary to relate the velocities to the flow rate.

Further, the shells are divided into two groups according to the flow velocities associated with them by defining a limit velocity $v_l = A/T_0$. Thus, two groups of shells are defined:

Slow shells, the contribution of one shell of this group to the Doppler spectrum being:

$$SS_m = \rho_m(A - v_m T_0)P(f_m, N, N) + \frac{2 v_m \rho_m T_0}{N} \sum_{j=1}^{N-1} P(f_m, j, N)$$

Fast shells, the contribution of one shell of this group to the Doppler spectrum being:

$$SF_m = \rho_m A\left(\frac{T_0}{tt_m} - 1\right) P(f_m, w_m, N) + \frac{2\rho_m A}{w_m} \sum_{j=1}^{w_m - 1} P(f_m, j, N)$$

Where
$w_m = tt_m \cdot f_s$ and P is a function for calculating the spectral contribution. Consequently, the total Doppler spectrum is the sum of contributions and expressed as:

$$ST = \sum_{m=0}^{m_t - 1} SS_m + \sum_{m=m_t}^{M-1} SF_m$$

Wherein $m_t$ is the last "slow" shell and M−1 is the total number of spectra.

Estimation of the Flow Rate

As seen above the M concentric shells are each associated with a velocity $v_m$ so that a discretized velocity profile of M velocities $v_0, v_1, \ldots v_{M-1}$ is obtained.

The resolution $v_S$ of this discretization in speed, which corresponds to the difference between two consecutive values of the vector $v_0, v_1, \ldots, v_{M-1}$, depends indirectly on the maximum speed $v_{M-1}$ and the number of concentric shells M. For a fixed number of shells, the higher the maximum speed $v_{M-1}$, the higher the speed resolution.

This can be seen with the following formula (where round up means "round to the next integer"):

$$M = \text{roundup}\left(\frac{v_M - 1}{v_s}\right)$$

Now the resolution $v_S$ is to be calculated.

Each frequency $f_m$ of the modeled Doppler Power Spectrum corresponds to a speed $v_m$ via the Doppler equation:

$$f_m = \frac{v_m f_e \cos(\theta)}{c}$$

The modeled Doppler Power Spectrum itself has a frequency resolution $f_r$. This frequency resolution is taken as equal to the frequency resolution of the experimental Doppler Power Spectrum, which is equal to the inverse of the acquisition time $T_0$, thus: $f_r = 1/T_0$.

This frequency resolution can be converted into a velocity resolution $v_S$ by using Doppler equation:

$$v_S = \frac{c f_r}{\cos(\theta) f_e}$$

The maximum speed depends on the flow rate imposed at the inlet:

$$Q_V = \frac{\pi R^2}{2} v_{M-1}$$

Where R is the radius of the tube and $v_{M-1}$ is the maximum speed.

In the same way as above, this equation can be expressed as a function of the maximum frequency of the modeled Doppler Power Spectrum (DPS) using the Doppler formula:

$$Q_V = \frac{\pi R^2}{2} \frac{c f_{M-1}}{\cos(\theta) f_e}$$

The latter equation represents the relation between the volume flow set at the input and the maximum frequency of the Doppler Power Spectrum. This relationship makes it possible to estimate the flow rate by comparing experimental DPS to modeled DPS.

Figure 5A:
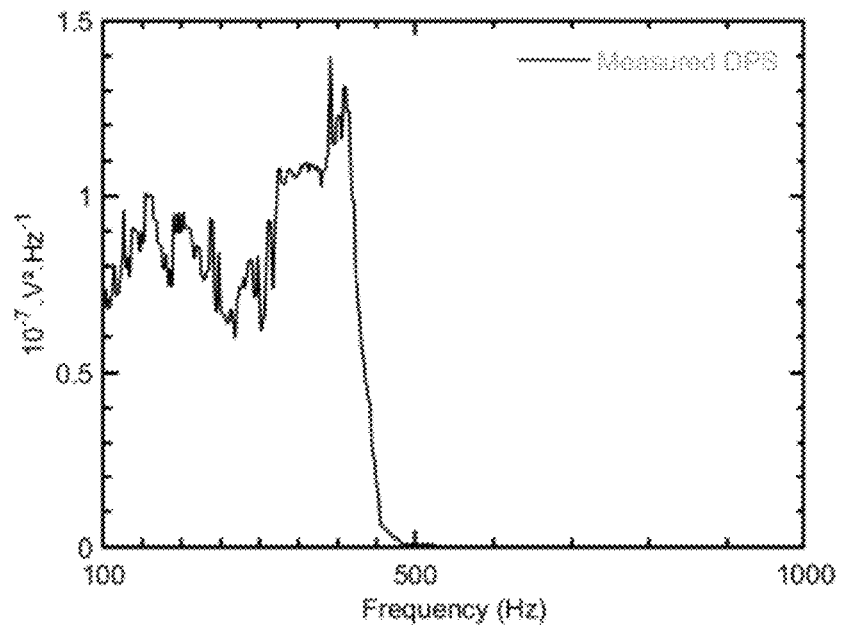
FIGS. 5a to 5c are diagrams corresponding to steps of the method for determining a fluid flow rate according to the invention, using, e.g., the measurement device of FIG. 1.
Figure 5B:
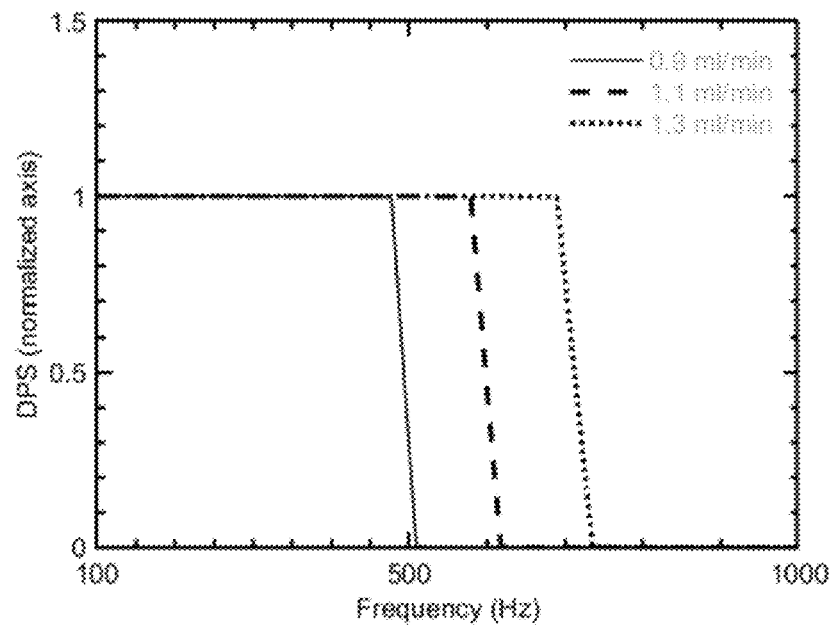

This comparison may be made in different manners. For example, a modeled DPS may be fitted with an acquired DPS. Another manner is to compare the experimentally acquired DPS to a set of theoretical DPS calculated by using the model discussed above. FIGS. 5a and 5b illustrate such a comparison. The acquired DPS of FIG. 5a is compared to a database of theoretical DPS of FIG. 5b.

In order to find the corresponding theoretical DPS, the fitting may be optimized by any appropriate method.

Figure 5C:
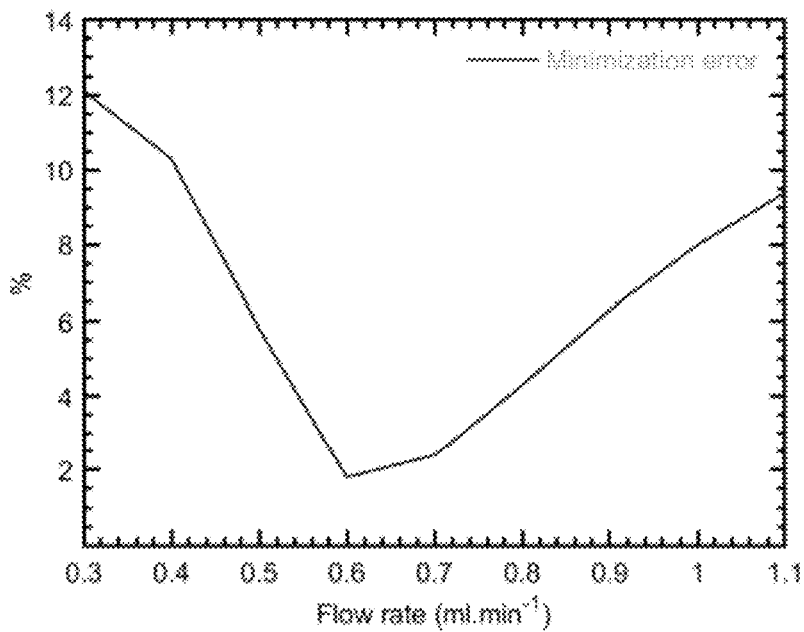

According to an advantageous embodiment, the optimization uses an optimization algorithm which minimizes a cost function. In particular, the flow rate Q may be determined as the value corresponding to:

$$\min \|S_{th}(Q) - S\|$$

where S is the acquired DPS, and $S_{th}(Q)$ is the theorical DPS which is a function of the flow rate Q. FIG. 5c illustrates the minimization of the cost function obtained from the acquired DPS of FIG. 5a and the theoretical DPS of FIG. 5b. The value corresponding to $\min \|S_{th}(Q) - S\|$ is 0.6 mL/min, which is the value of the flow rate Q determined according to the invention.

This determination of the minimum value is preferably performed using a calculation means implementing the optimization algorithm.

According to another embodiment, the minimization of the cost function may be expressed as:

$$\min \|S_{th}(Q, A, R) - S\|$$

where S is the acquired DPS, and $S_{th}(Q, A, R)$ is the theorical DPS which is a function of the flow rate Q, the width A of the intersection of the ultrasonic beam and the chamber (tube) and the radius R of the chamber.

In practice, in addition to the estimation of the flow rate Q, the method and device according to the invention can also provide an estimation of the parameters A and R. In this way, it is possible to take into account possible fluctuations of the parameters A and R, thus allowing a very precise calibration of the measurement method and device.

Experimental Example

For the purpose of the test, a sample of whole human blood diluted to 8% hematocrit is injected into the chamber 2 of the measurement device 1 of FIG. 1. A flow rate is imposed at the input of the chamber 2 by a syringe pump. Then, the input flow rate is varied from 0.5 m/min to 1.5 m/min by steps of 0.1 m/min. For each input flow rate value, an ultrasound beam is generated by the first transducer 61 of the probe 6 and Doppler-shifted ultrasound signals are collected by the second transducer 62 of the probe.

Ten acquisitions of 10 s are made for each input flow rate.
The fixed parameters of the system are:
Scatterers density: $p_m = 1$ for any m value
Signal frequency: $f_e = 8$ MHz
Acquisition time: $T_0 = 10$ s
Number of samples: N=200000000
Sampling frequency: $F_s = 20$ Mhz
Speed of sound in blood: c=1570 m/s
Doppler angle: θ=40°

The parameters $tt_m$, $f_m$ et $v_m$ are implicitly calculated in the model but all three are combinations of the previous parameters and therefore do not provide additional information.

Finally, the parameters A (Insonated region width (m)); R (tube radius (m)), and Q (Flow rate (mL/min)) are determined using algorithms of the calculation module as described above.

Figure 6:
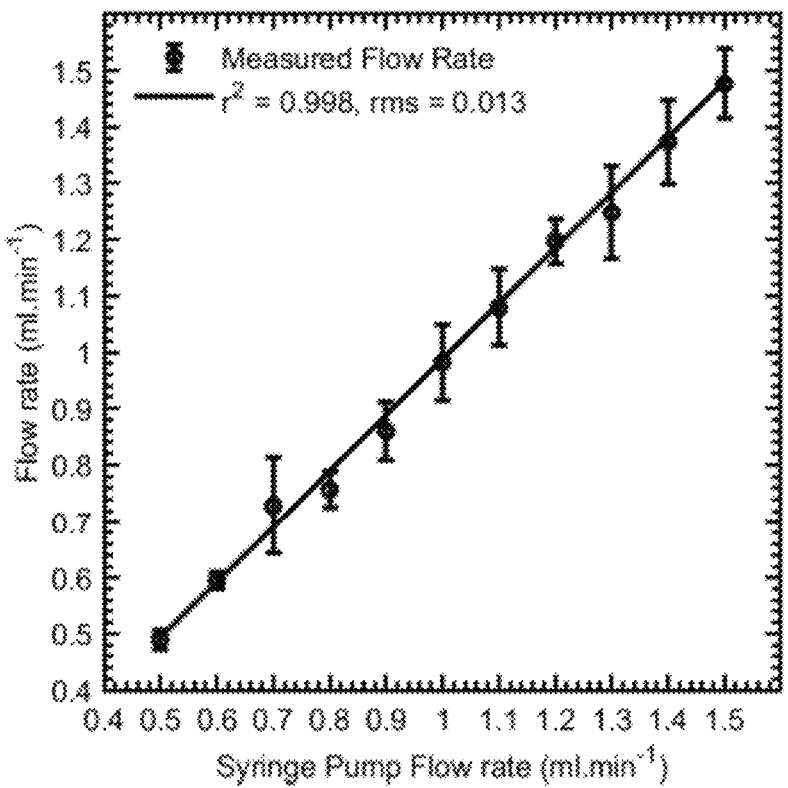
FIG. 6 is a diagram showing a comparison between the fluid flow rate determined according to the invention and an imposed input fluid flow rate.

FIG. 6 shows the comparison of the flow rate estimated according to the method described above and the flow rate imposed by the syringe pump. The ten acquired values of the flow rate were averaged.

The mean difference found between the flow rate of the syringe pump and the estimated flow rate is 1.3%.

Further, an average value of 3.9.10-4 m was determined for the radius R of the tube 3 (whereas the tube constructor indicates a value of 3.8.10-4 m) and an average value of 4.10-3 m for the beam width A.

In other non-shown examples, for the same values of input flow rate on the same blood sample, the acquisition time has been decreased to about 2 seconds without significantly altering the accuracy of the method.

Determination of Scatterers Concentration

Principle

In addition to providing the flow rate, the Doppler Power Spectrum (DPS) also provides information about the concentration of diffusing particles (scatterers) within the fluid flow. Indeed, the amount of total energy present in the Doppler Power Spectrum is directly dependent on the number of scatterers present in the fluid flow. To express this dependence mathematically, the integral of Doppler Power Spectrum is used over a frequency band delimited by a maximum frequency $f_{max}$ ($f_{max}$ being higher than the maximum frequency of the Doppler spectrum). By using this integral, all the energy present in the Doppler Power Spectrum is well quantified.

Therefore, by determining the dependency law of the integral of DPS on the number of scatterers, the concentration of the scatterers may be extracted by comparing the integral of the DPS to a calibration function.

Figure 7:
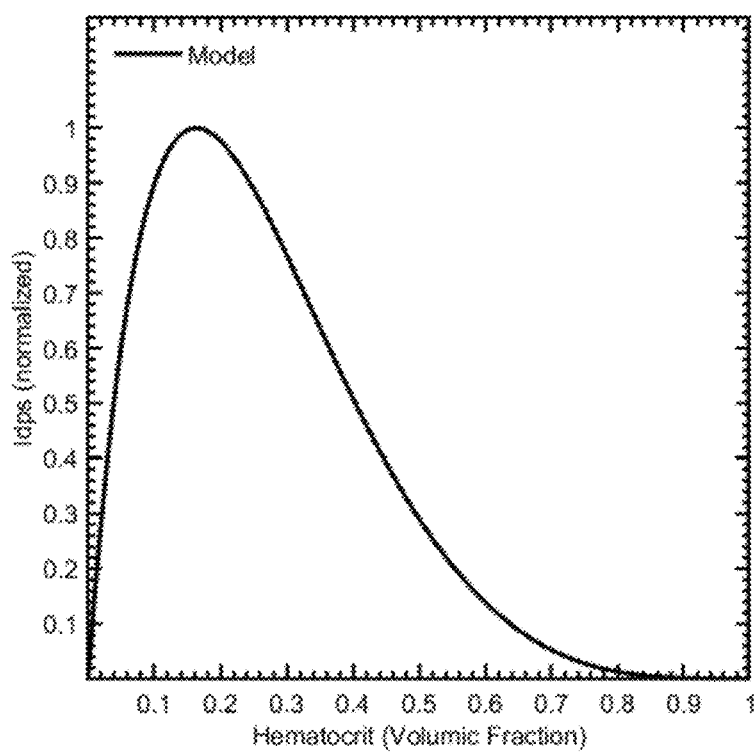
FIG. 7 is a diagram showing a theoretical variation of an integral of the normalized Doppler Power Spectrum as a function of the hematocrit (or volumic concentration of red blood cells).

FIG. 7 illustrates an explicative example of such determination in the case of blood. It is common knowledge to use the term "hematocrit" to refer to the volumic concentration of red blood cells. More precisely, the hematocrit H is defined as the volume fraction of red blood cells in blood. The relationship between the hematocrit H and the integral $I_{DPS}$ of the DPS has the profile shown in FIG. 7. This theoretical relationship is used herein only for the sake of illustration of the method.

As can be seen in FIG. 7, in the range 0% to 10% of hematocrit (H), the evolution of the integral $I_{DPS}$ is linear and thus can be expressed in this range as:

$$I_{DPS} = a \cdot H$$

wherein «a» is a constant which can be determined experimentally by measuring the variations $I_{DPS}$ as a function of H. This determination is a calibration. Further, in the hypothesis that the dimensions and parameters of the experimental device do not change, it is possible to determine H via measurement of $I_{DPS}$.

Of course, this method may be generalizable to non-linear functions. The necessary condition is that the calibration must be sufficiently precise to allow approximation of the function without errors.

Estimation of the Concentration

The principle remains the same as for the measurement of the flow rate except that it relates here to the integrals of the Doppler spectra as explained previously. The comparison is made between the integral of the theoretical DSP and a function determined by a calibration linking the theoretical DSP to the concentration of fluid particles (hematocrit in the case of blood).

The steps of the calibration are the following:
- a number of k DPS acquisitions are made at a value of the hematocrit ($H_n$) that give a total of k DSP Doppler (k being equal or superior to 1);
- the k experimental DPS are averaged, then the method for determining flow rate discussed above is used for determining the theoretical spectrum corresponding to the averaged DPS;
- the integral of the theoretical spectrum is chosen as a calibration value of the theoretical integral $I_{th}(H_n)$;
- the preceding steps are repeated a sufficient number of times so as to minimize the variance. A series of theoretical integrals are then obtained, which are averaged to obtain the final value $I_{th}(H_n)$;
- this calibration is performed for several hematocrit values $H_n$ in order to extrapolate a continuous calibration function $I_c(H)$.

Finally, the measurement of the hematocrit (H) consists in finding the value H such that:

$$\min \|I_c(H) - I_{th}\|$$

wherein $I_{th}$ is the integral of the theoretical DPS adjusted to the experimental Doppler DPS and $I_C$ the calibration function.

The calibration is given here in the case of blood, but the same method may be applied for other fluids.

Experimental Example

First, measurements were performed for the following hematocrit values: 2, 4.1, 5.8, 7.4, 9.8, 11.3, 13.3, 15.2, 17.8.

The values are expressed in % (% of blood volume taken by red blood cells) and are derived from measurements made with a Pentra ABX (a hematocrit measuring device) which serves as a standard.

The rest of the parameters are the same as for the example of flow rate measurement described above.

Secondly, calibration was performed by taking 20 acquisitions (k=20) of 10 s for each hematocrit value mentioned above. The integrals of the theoretical spectra were then averaged over the 20 acquisitions for each hematocrit.

The flow rate set at the inlet was 1.5 mL/min and the calibration was done on the theoretical spectra adjusted to the experimental spectra by the flow measurement method.

Figure 8:
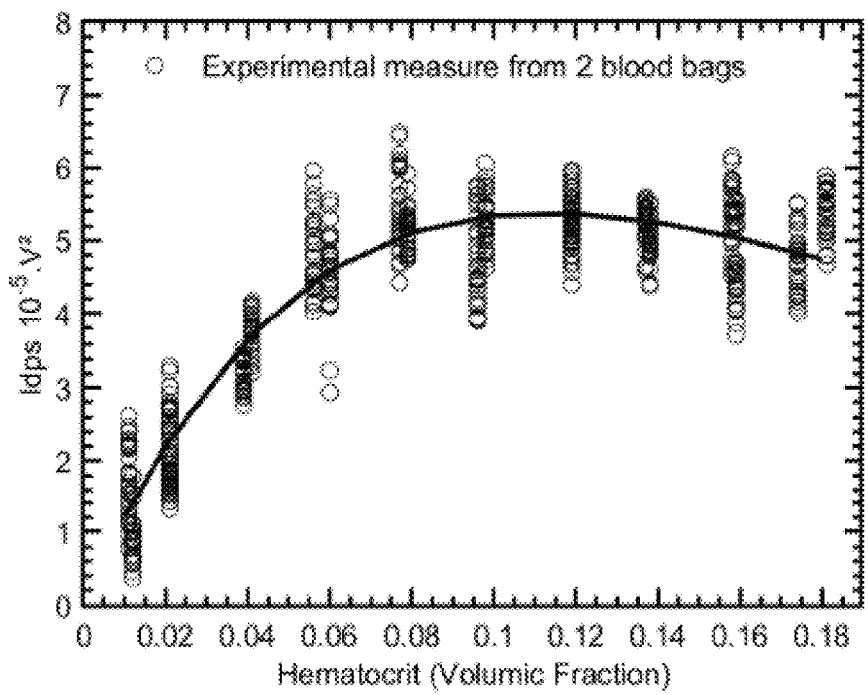
FIG. 8 is a diagram showing a step of the method for determining the hematocrit (or volumic concentration of red blood cells) of blood flowing in a chamber.

FIG. 8 shows the result of the calibration. The averaged values of $I_{DPS}$ are represented as discrete ranges. The continuous curve is the function extrapolated from the calibration which is then used to perform the minimization ($\min \|I_c(H) - I_{th}\|$) in order to estimate the hematocrit H.

Figure 9:
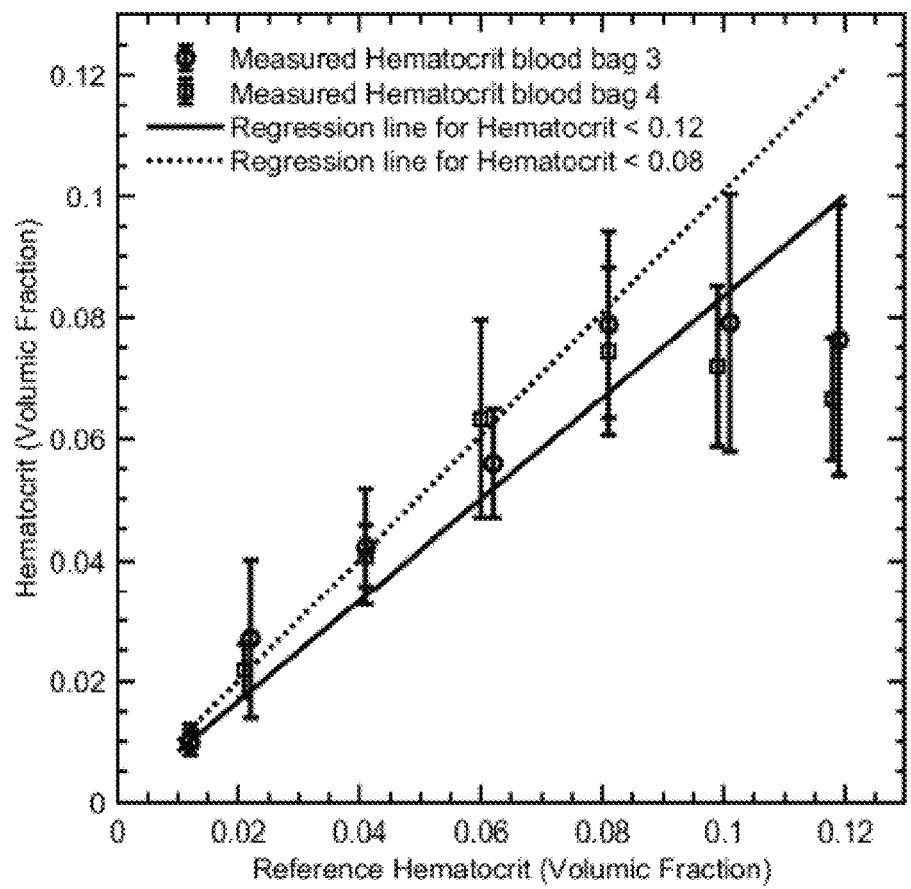
FIG. 9 is a diagram showing a comparison between the hematocrit (or volumic concentration of red blood cells) determined according to the invention and hematocrit measured by means of a control device.

FIG. 9 shows the result of the volumic concentrations (Hematocrit) determined from the minimization and compared to the reference values measured by the Pentra ABX device. As can be seen, in the range 0 to 10%, the hematocrits determined by the method of the invention are close to the reference values.

However, above 10%, the measurement of the hematocrit becomes imprecise. This can be explained from the calibration curve in FIG. 8, where it can be seen that, above 10%, on the one hand the standard deviation becomes high, and on the other hand the calibration relationship saturates.

This problem can be overcome by optimizing the parameters of the measuring system (resolution and dynamic range, frequency, acquisition time, voltage emitted . . . ) and performing a more rigorous calibration.

Measurements below 10% are more accurate and the correct measurement range can be extended beyond 10%.

Nevertheless, this measurement is already a good proof of concept of the method which shows that an accurate measurement of the volumic concentration is possible as long as the calibration is correctly carried out for the targeted volumic concentration range.

Figure 10:
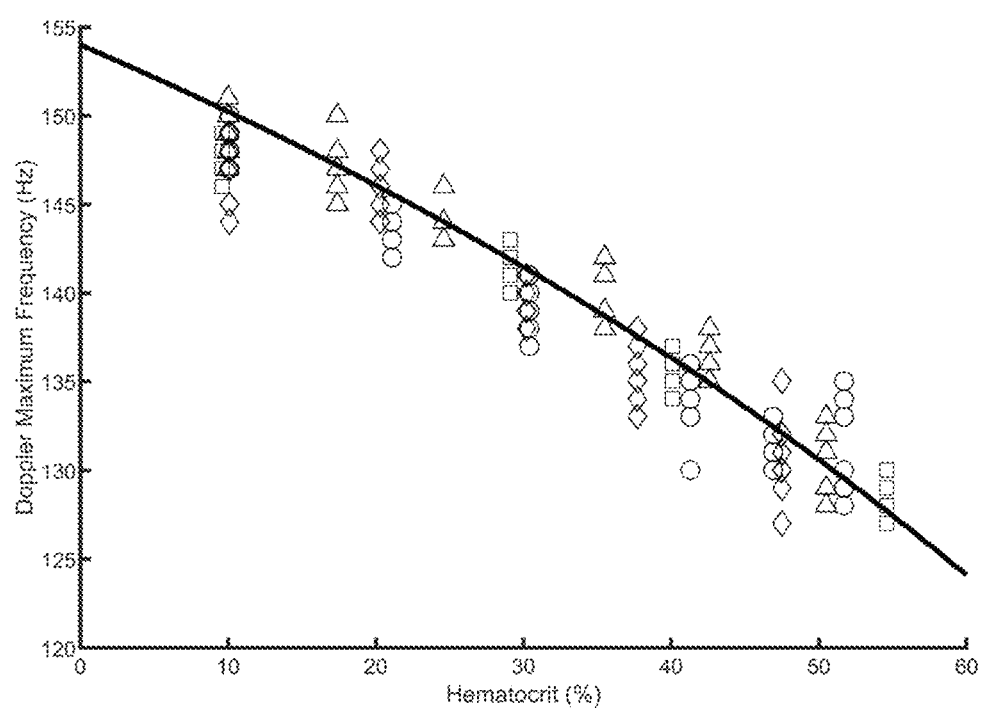
FIG. 10 is a graph showing the doppler maximum frequency in Hz as a function of the Hematocrit %.

FIG. 10 shows the relationship between the maximum Doppler frequency in Hz and the hematocrit percentage. Said percentage has been evaluated on four different blood bag, each bag corresponding to a type of marker in the FIG. 10 and the line drawn is the extrapolated relation from the four blood bags.

Based on this relationship one can derive the hematocrit percentage from the maximum Doppler frequency in Hz.

Finally, while various embodiments have been described and illustrated, the detailed description is not to be construed as being limited hereto. Various modifications can be made to the embodiments by those skilled in the art without departing from the true spirit and scope of the disclosure as defined by the claims.

The invention claimed is:

1. A method for determining a flow rate of a fluid flowing in a chamber and a concentration of particles of the fluid, the method comprising steps of:
    producing with a first transducer an ultrasound beam of a frequency that is in a scattering frequency range of said particles so that all fluid components traveling through an intersection region between the ultrasound beam and the chamber are insonated by the first transducer to create an insonated region of the chamber;
    receiving with a second transducer Doppler-shifted ultrasound signals generated by the fluid components in said insonated region;
    acquiring the ultrasound signals received by the second transducer, during an acquisition time;
    obtaining a Doppler Power Spectrum of the acquired ultrasound signals;
    determining the flow rate of the fluid flowing in the chamber and the concentration of said particles of the fluid in the insonated region by adjustment between the obtained Doppler Power Spectrum and a model expressing the Doppler Power Spectrum as a function of the flow rate of the fluid in the insonated region, the concentration of said particles of the fluid in the insonated region, a cross-sectional area of the chamber taken perpendicular to a flow direction of the fluid, a width of the intersection between the ultrasound beam and the chamber taken parallel to the flow direction.

2. The method according to claim 1, wherein the Doppler-shifted ultrasound signals are generated by the fluid components in said insonated region of the chamber while the concentration of said particles of the fluid in the insonated region has a known concentration value, and
    the method comprises a step of determining the flow rate of the fluid flowing in the chamber by adjustment between the obtained Doppler Power Spectrum and a model expressing the Doppler Power Spectrum as a function of the flow rate of the fluid in the insonated region of the chamber, the concentration of said particles of the fluid in the insonated region, the cross-sectional area of the chamber taken perpendicular to the flow direction, the width of the intersection between the ultrasound beam and the chamber taken parallel to the flow direction, with the concentration of said particles of the fluid in the insonated region being fixed at said known concentration value.

3. The method according to claim 1, wherein the Doppler-shifted ultrasound signals are generated by the fluid components in said insonated region of the chamber, and the flow rate of the fluid flowing in the chamber has a known flow rate value, and the method comprises a step of determining the concentration of said particles of the fluid in the insonated region by adjustment between the obtained Doppler Power Spectrum and a model expressing the Doppler Power Spectrum as a function of the flow rate of the fluid in the insonated region of the chamber, the concentration of said particles of the fluid in the insonated region, the cross-sectional area of the chamber taken perpendicular to the flow direction, the width of the intersection between the ultrasound beam and the chamber taken parallel to the flow direction, with the flow rate of the fluid in the insonated region of the chamber being fixed at said known flow rate value.

4. The method according to claim 1, comprising steps of:
calculating an integral of the obtained Doppler Power Spectrum over a frequency range including a maximum frequency of the Doppler Power Spectrum;
determining the concentration of particles of the fluid in the insonated region by adjustment between the integral of the obtained Doppler Power Spectrum and a model expressing the integral of the Doppler Power Spectrum as a function of the concentration of said particles of the fluid in the insonated region.

5. The method according to claim 1, wherein the fluid is blood and a volumic concentration of red blood cells is determined by calculating a maximum frequency of the obtained Doppler Power Spectrum.

6. The method according to claim 1, wherein the adjustment is realized using an optimization algorithm comprising a minimization of a cost function expressed with a predefined norm.

7. The method according to claim 1, wherein the Doppler Power Spectrum of the acquired ultrasound signals is obtained using a demodulation method.

8. A method for determining a concentration of a first group of particles and a concentration of a second group of particles of a fluid, the particles of the first group and the particles of the second group being particles having scattering frequency ranges at least partially not overlapping, the method comprising:
determining the concentration of the first group of particles according to the method of claim 1, by producing a first ultrasound beam of a first frequency;
determining the concentration of the second group of particles or a total concentration of the first and second groups of particles according to said method, by producing a second ultrasound beam of a second frequency.

9. The method according to claim 8, wherein the fluid is blood, the particles of the first group are red blood cells and the particles of the second group are platelets, wherein the first frequency, which is suitable for the determination of the concentration of red blood cells, is lower than the second frequency, which is suitable for the determination of the total concentration of red blood cells and platelets.

10. A computer program comprising instructions for the implementation of the calculation steps of a method according to claim 1 when the program is executed by a computer.

11. A non-transitory computer readable medium comprising instructions for the implementation of the calculation steps of a method according to claim 1 when the instructions are executed by a computer.

12. A measurement device for determining a flow rate of a fluid flowing in a chamber and/or a concentration of particles of the fluid, comprising:
a first transducer configured to produce an ultrasound beam of a frequency in a scattering frequency range of said particles so that all fluid components traveling through an intersection region between the ultrasound beam and the chamber are insonated by the first transducer to create an insonated region in the chamber,
a second transducer, arranged at a Doppler angle to the flow direction and configured to receive Doppler-shifted ultrasound signals generated by the fluid components in said insonated region of the chamber;
an acquisition module for acquiring the ultrasound signals received by the second transducer during an acquisition time;
a calculation module configured to calculate a Doppler Power Spectrum of the ultrasound signals acquired by the acquisition module and to determine the flow rate of the fluid flowing in the chamber and the concentration of said particles of the fluid by adjustment between the calculated Doppler Power Spectrum and a model expressing the Doppler Power Spectrum as a function of the flow rate of the fluid in the insonated region, the concentration of said particles of the fluid in the insonated region, a cross-sectional area of the chamber taken perpendicular to a flow direction of the fluid, a width of the intersection between the ultrasound beam produced by the first transducer and the chamber taken parallel to the flow direction.

13. The measurement device according to claim 12, wherein the first transducer is configured to produce an ultrasound beam selectively at a first frequency and at a second frequency distinct from the first frequency, at least one of the first and second frequencies being in a non-overlapping portion between the scattering frequency ranges of two groups of particles.

14. A separation device comprising:
a cavity configured to receive a flow of a fluid comprising particles,
at least one inlet at a first end of the cavity,
at least two outlets at a second end of the cavity, comprising at least one concentrate-outlet and at least one filtrate-outlet,
wherein the separation device further comprises at least one measurement device according to claim 13.

* * * * *